United States Patent
McAdams et al.

(10) Patent No.: US 9,322,811 B2
(45) Date of Patent: Apr. 26, 2016

(54) ZERO DEAD VOLUME ROBUST FLUIDIC CONNECTION SYSTEM

(71) Applicants: Michael John McAdams, Los Gatos, CA (US); Milton Liu, Burlingame, CA (US); George N. Proper, Milpitas, CA (US)

(72) Inventors: Michael John McAdams, Los Gatos, CA (US); Milton Liu, Burlingame, CA (US); George N. Proper, Milpitas, CA (US)

(73) Assignee: DIONEX CORPORATION, Sunnyvale, CA (US)

(*) Notice: Subject to any disclaimer, the term of this patent is extended or adjusted under 35 U.S.C. 154(b) by 164 days.

(21) Appl. No.: 13/674,330

(22) Filed: Nov. 12, 2012

(65) Prior Publication Data

US 2014/0130580 A1    May 15, 2014

(51) Int. Cl.
*G01N 30/00*    (2006.01)
*F16L 19/02*    (2006.01)
*B01L 3/00*    (2006.01)
(Continued)

(52) U.S. Cl.
CPC .............. *G01N 30/00* (2013.01); *B01L 3/563* (2013.01); *F16L 19/02* (2013.01); *F16L 19/065* (2013.01); *G01N 30/6026* (2013.01); *B01L 3/565* (2013.01); *B01L 2300/0838* (2013.01); *G01N 30/16* (2013.01); *G01N 30/6004* (2013.01); *G01N 30/6039* (2013.01)

(58) Field of Classification Search
CPC ........ F16L 19/02; F16L 19/065; B01L 3/563; G01N 30/00; G01N 30/6026; G01N 30/6004; G01N 30/16; G01N 30/6039
USPC ............ 73/61.52, 23.35, 61.56; 96/101, 106; 210/656, 198.2; 285/357, 24; 29/2.15; 81/121.1
See application file for complete search history.

(56) References Cited

U.S. PATENT DOCUMENTS

| 2,998,984 A | 9/1961 | Gressel |
| 3,722,925 A | 3/1973 | Robbins |

(Continued)

FOREIGN PATENT DOCUMENTS

| CN | 86108054 A | 6/1987 |
| CN | 2087340 U | 10/1991 |

(Continued)

OTHER PUBLICATIONS

BASF Corporation, "Innovations in Laser Welding of Thermoplastics: This Advanced Technology is Ready to be Commercialized," Jan. 1, 2002, 21 pages, copyright 2003.

(Continued)

*Primary Examiner* — Daniel S Larkin
(74) *Attorney, Agent, or Firm* — Victor Johnson (57) ABSTRACT

A fluidic connection system may comprise a port which includes a capillary tube receptacle with an end seal face and a threaded wall. The fluidic connection system may also comprise a capillary tube that includes a front end face for sealingly abutting against the end seal face of the port. On the capillary tube, a flange may be affixed at a distance from the front end face of the capillary tube. The fluidic connection system may further comprise a fitting nut that includes an axial hole to allow the capillary tube to pass therethrough and a matching threaded wall corresponding to the threaded wall of the port. The fitting nut may be slidably coupled with the capillary tube behind the flange. The distance at which the flange is affixed may be predetermined such that when the flange is pushed forward by the fitting nut, the front end face of the capillary tube abuts directly against the end seal face of the port.

20 Claims, 8 Drawing Sheets

(51) Int. Cl.
*F16L 19/065* (2006.01)
*G01N 30/16* (2006.01)
*G01N 30/60* (2006.01)

(56) References Cited

U.S. PATENT DOCUMENTS

| | | | |
|---|---|---|---|
| 3,880,452 | A | 4/1975 | Fields |
| 4,619,473 | A | 10/1986 | Someya |
| 5,669,637 | A | 9/1997 | Chitty et al. |
| 5,709,413 | A | 1/1998 | Salyers |
| 6,131,963 | A | 10/2000 | Williams et al. |
| 6,494,500 | B1 | 12/2002 | Todosiev et al. |
| 6,851,729 | B2 | 2/2005 | Gibson |
| 8,006,367 | B1 | 8/2011 | Best |
| 8,037,788 | B2 | 10/2011 | Proper |
| 8,394,275 | B2 | 3/2013 | Benevides et al. |
| 8,569,070 | B2 * | 10/2013 | Ellis et al. ............. 436/161 |
| 8,702,130 | B1 * | 4/2014 | Zelechonok ............ 285/342 |
| 2006/0038402 | A1 | 2/2006 | Norman et al. |
| 2007/0089603 | A1 | 4/2007 | Emmons et al. |
| 2010/0018359 | A1 * | 1/2010 | Proper ................. 81/121.1 |
| 2010/0156089 | A1 * | 6/2010 | Zelechonok et al. ...... 285/24 |
| 2011/0173786 | A1 * | 7/2011 | Moshfegh et al. ....... 29/2.15 |
| 2011/0198843 | A1 | 8/2011 | Ikenoya et al. |
| 2011/0278214 | A1 * | 11/2011 | Benevides et al. ..... 210/198.2 |
| 2011/0298210 | A1 * | 12/2011 | Hochgraeber et al. ... 285/357 |
| 2012/0024411 | A1 | 2/2012 | Hahn et al. |
| 2012/0061955 | A1 | 3/2012 | Hochgraeber et al. |
| 2012/0223520 | A1 | 9/2012 | Graham |
| 2014/0145437 | A1 | 5/2014 | Burger et al. |

FOREIGN PATENT DOCUMENTS

| | | |
|---|---|---|
| CN | 1389726 A | 1/2003 |
| CN | 101017161 A | 8/2007 |
| DE | 10028503 | 12/2000 |
| DE | 102008059897 A1 | 6/2010 |
| DE | 102009022368 B | 11/2010 |
| DE | 102011050037 B3 | 6/2012 |
| EP | 0224188 B1 | 11/1989 |
| EP | 0379401 A1 | 7/1990 |
| GB | 2482175 A | 1/2012 |
| JP | 61191589 U1 | 11/1986 |
| JP | 07167357 | 7/1995 |
| WO | 9936722 A1 | 7/1999 |
| WO | 2009088663 A1 | 7/2009 |
| WO | 2010063267 A1 | 6/2010 |
| WO | 2012010222 A1 | 1/2012 |
| WO | 2012148793 A1 | 11/2012 |
| WO | 2012149930 | 11/2012 |

OTHER PUBLICATIONS

Solvay Specialty Polymers, "Laser Welding Guide: Amodel polyphthalamide (PPA)," Technical Bulletin, 4 pages, copyright 2012.

Application No. 201310566413.1, Chinese Office Action mailed Oct. 22, 2014.

Chinese Application No. 201310566413.1, Search Report dated Oct. 10, 2014.

* cited by examiner

ZERO DEAD VOLUME ROBUST FLUIDIC CONNECTION SYSTEM

FIELD OF INVENTION

The present invention generally relates to a fluidic connection system for use in chromatography, and more specifically to a zero dead volume robust fluidic connection system for use in high-performance liquid chromatography.

DESCRIPTION OF RELATED ART

Connection systems are used in chromatography for connecting capillary tubes in ports, columns or other fluidic components. To obtain optimal separations from a mixture of compounds, connection systems should be configured to reduce or eliminate the dead volume that may exist in between the two capillary tubes, because the dead volume can adversely impact the performance of a chromatographic system. For example, a dead volume can have significant effects on chromatographic peak broadening, which in some cases may result in errors in identifying, quantifying or purifying individual components of the mixture. In addition, there is a risk of leakage, which is very difficult to detect under capillary flow rates. Therefore, it is desirable to have a zero dead volume seal between all fluidic components in chromatography in order to achieve best or optimum chromatographic performance.

Ideally, to have a zero dead volume seal between two fluidic components, the sealing position should be realized in the plane in between the opposing end surfaces of the fluidic components. Specifically, a front end surface of a fluidic component should abut directly against a rear end surface of another fluidic component. In case of capillary tubes, the plane in between the two opposing surfaces should also be perpendicular to the longitudinal axis of the capillary tubes and both surfaces must be flat and defect free.

Most conventional fittings utilize a ferrule for sealing that, for example, can be found in U.S. Pat. Nos. 6,131,963 and 6,851,729. The sealing position achieved by the ferrule, however, is offset and away from the end surface of the capillary tube. For the situation where the ferrule is permanently attached to the capillary tube, a user can inadvertently create a void volume by incorrectly setting the ferrule offset position. As another possibility, a user can inadvertently switch a capillary tube, which already has a permanently attached ferrule, to a fitting that requires a different ferrule set distance. In addition to inadvertent user error, ferrules and capillaries can slip, especially when the fittings are subjected to high pressures, as used in ultra-performance liquid chromatography. This may also compromise the performance or efficiency of chromatography.

A different type of conventional fitting includes a ferrule that is not permanently attached to the capillary tube and is set to a proper offset position by a user. In this situation, a user must re-set the ferrule offset position when it is re-connected to a fitting. With resettable ferrules, a user can also inadvertently create a void volume by failing to set the ferrule to the proper offset position at the initial installation or when it is re-set.

Other fittings utilize a trumpet-shaped structure at the end of a capillary tube or a sealing element that has a hollow cylindrical construction to achieve a desired seal. Exemplars of such fittings can be found in U.S. Patent Application Publication No. 2011/0298210 to Hochgraeber et al. and U.S. Patent Application Publication No. 2012/0061955, which disclose a plug unit and connection system for connecting capillary tubes, especially for high-performance liquid chromatography. Such fittings typically require precision machining of the receptacle to form a liquid tight seal with zero dead volume, which causes the manufacturing processes to be expensive and relatively complex.

Fitting for connecting fluidic components in chromatography can be tightened by hand or with tools. However, conventional fittings that use a ferrule need to be tightened correctly to ensure a proper seal. If not tightened enough, the capillary tube may pop out of the fitting port under pressure and the fittings will need to be removed and reassembled. On the contrary, if overly tightened, the ferrule can be crimped tightly onto the sealing port, making it very difficult to remove or be reusable.

Applicant believes that it would be an advantage for the trumpet-shaped structure or the sealing element that has a hollow cylindrical construction to be made of PEEK and be re-usable. However, under certain circumstances, such fittings can be deformed causing the trumpet-shaped structure or sealing element to flow into the threaded portion of the fitting. Because of the PEEK in the threaded portion, the fitting assembly would not suitable for re-use and thus would be discarded after disconnection. In addition, under certain circumstances, the fitting assembly may be difficult to unscrew when there is PEEK material in the threaded portion. Applicant believes that there is a need for fitting assemblies that are more robust to overtightening so that the fitting assemblies can be re-used and thus reduce operational costs.

In light of the above, it is desirable to provide a connection system with a zero dead volume seal that overcome at least some of the above-mentioned challenges.

The information disclosed in this Background section is only for enhancement of understanding of the general background of the invention and should not be taken as an acknowledgement or any form of suggestion that this information forms the prior art already known to a person skilled in the art.

BRIEF SUMMARY

Various aspects of the present application are directed to provide a fluidic connection system that enhances chromatography performance by ensuring a zero dead volume and leakage free seal without using a ferrule.

One aspect of the present application is directed to provide a fluidic connection system including a port which includes a capillary tube receptacle with an end seal face and a threaded wall. The fluidic connection system also includes a capillary tube that includes a front end face for sealingly abutting against the end seal face of the port. On the capillary tube, a flange is affixed at a distance from the front end face of the capillary tube. The fluidic connection system further includes a fitting nut that includes an axial hole to allow the capillary tube to pass therethrough and a matching threaded wall corresponding to the threaded wall of the port. The fitting nut is slidably coupled with the capillary tube behind the flange. The distance at which the flange is affixed may be predetermined such that when the flange is pushed forward by the fitting nut, the front end face of the capillary tube abuts directly against the end seal face of the port.

Another aspect of the present application is directed to a plug for removably connecting a port with an end seal face. The plug includes a capillary tube that includes a front end face for sealingly abutting against the end seal face of the port. On the capillary tube, a flange is affixed a distance from the front end face of the capillary tube. The plug also includes a fitting nut that includes an axial hole to allow the capillary tube to pass therethrough and a matching threaded wall corresponding to a threaded wall of the port. The fitting nut is slidably coupled with the capillary tube behind the flange. The distance at which the flange is affixed may be predetermined such that when the flange is pushed forward by the fitting nut, the front end face of the capillary tube abuts directly against the end seal face of the port.

Still another aspect of the present application is directed to a chromatography system including a device that includes a port. The port includes a capillary tube receptacle with an end seal face and a threaded wall. The chromatography system further includes a connection line that includes a plug at one end for removably connecting the port in the device. The plug includes a capillary tube that includes a front end face for sealingly abutting against the end seal face of the port. On the capillary tube, a flange is affixed a distance from the front end face of the capillary tube. The plug also includes a fitting nut that includes an axial hole to allow the capillary tube to pass therethrough and a matching threaded wall corresponding to a threaded wall of the port. The fitting nut is slidably coupled with the capillary tube behind the flange. The distance at which the flange is affixed may be predetermined such that when the flange is pushed forward by the fitting nut, the front end face of the capillary tube abuts directly against the end seal face of the port. The device may be at least one of an eluent generator, a sample injection valve, a column, a suppressor, or a detector.

The fluidic connection system, the plug, and the chromatography system described above can be configured such that the most front face of the flange does not touch the port. More particularly, the most front face of the flange does not touch the port when the flange is pushed forward by the fitting nut, or when the front end face of the capillary tube contacts the end seal face of the port.

The methods and apparatuses of the present invention have other features and advantages which will be apparent from or are set forth in more detail in the accompanying drawings, which are incorporated herein, and the following Detailed Description, which together serve to explain certain principles of the present invention.

BRIEF DESCRIPTION OF THE DRAWINGS

In the drawings, like numerals describe similar components throughout the several views. Like numerals having different letter suffixes represent different instances of similar components. The drawings illustrate generally, by way of example, but not by way of limitation, various embodiments disclosed herein.

DETAILED DESCRIPTION

Reference will now be made in detail to various embodiments of the present invention(s), examples of which are illustrated in the accompanying drawings and described below. While the invention(s) will be described in conjunction with exemplary embodiments, it will be understood that present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

Figure 1A:
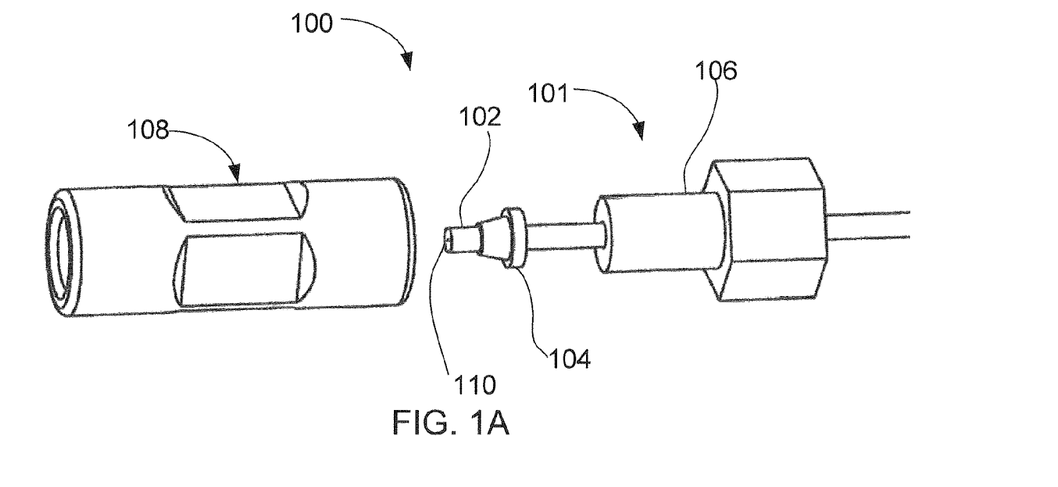
FIG. 1A illustrates an exemplary fluidic connection system in accordance with the present application.
Figure 1B:
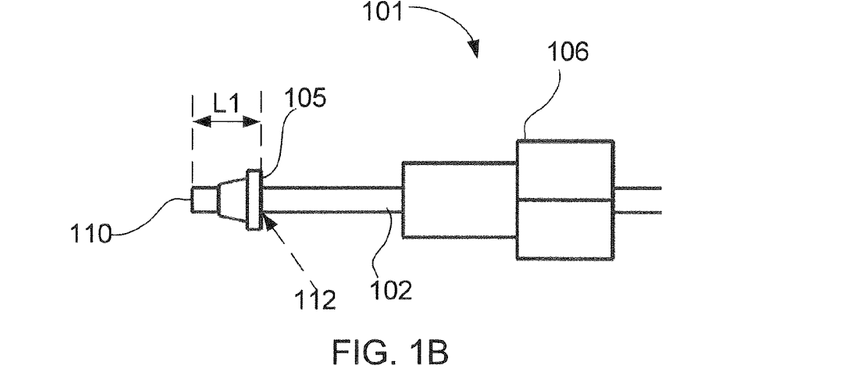
FIG. 1B illustrates an exemplary control of a distance in an exemplary fluidic connection system in accordance with the present application.
Figure 1C:
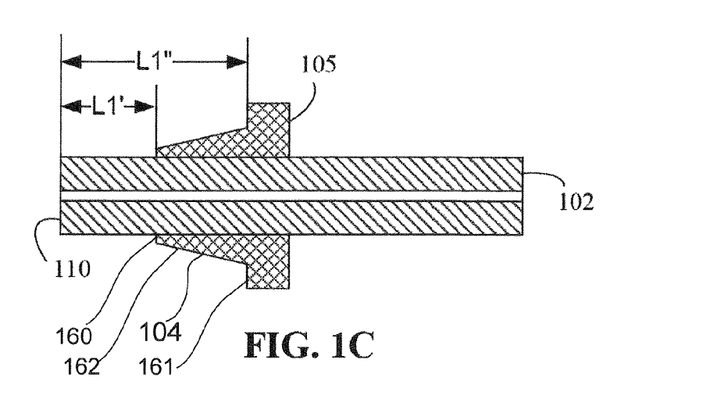
FIG. 1C illustrates another exemplary control of a distance in an exemplary fluidic connection system in accordance with the present application.
Figure 2:
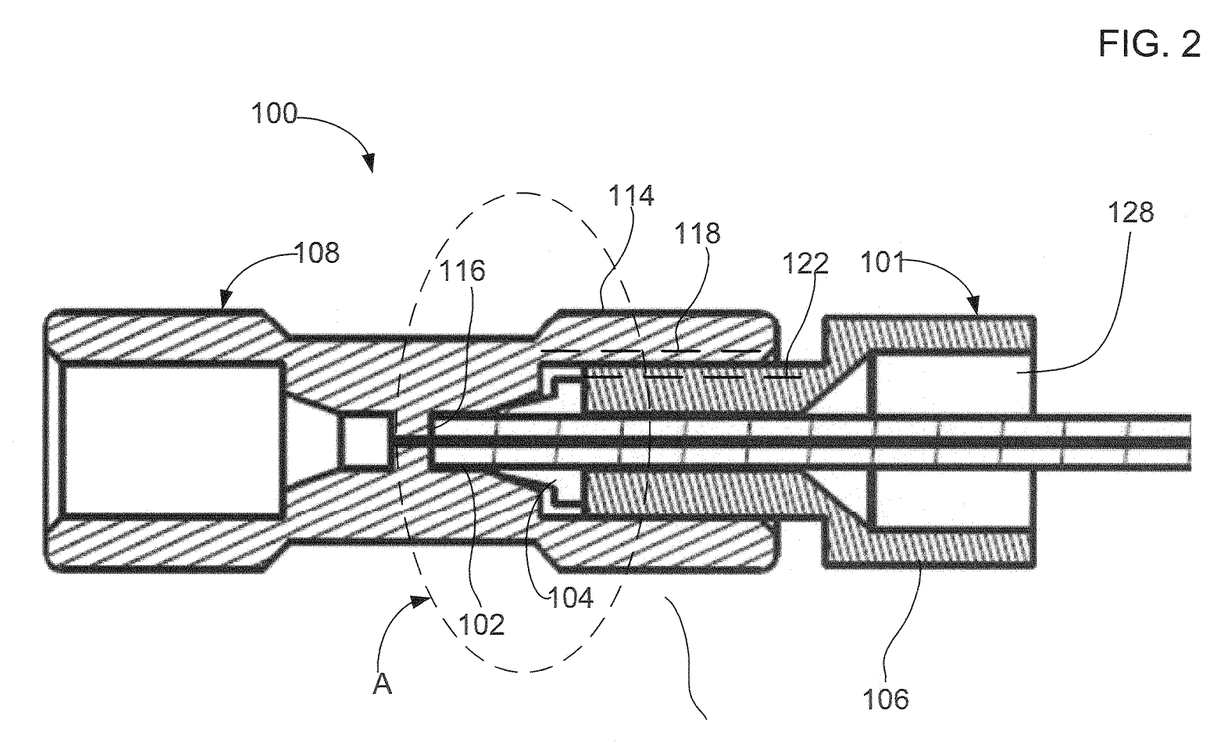
FIG. 2 illustrates a cross-sectional view of an exemplary fluidic connection system in accordance with the present application.
Figure 3A:
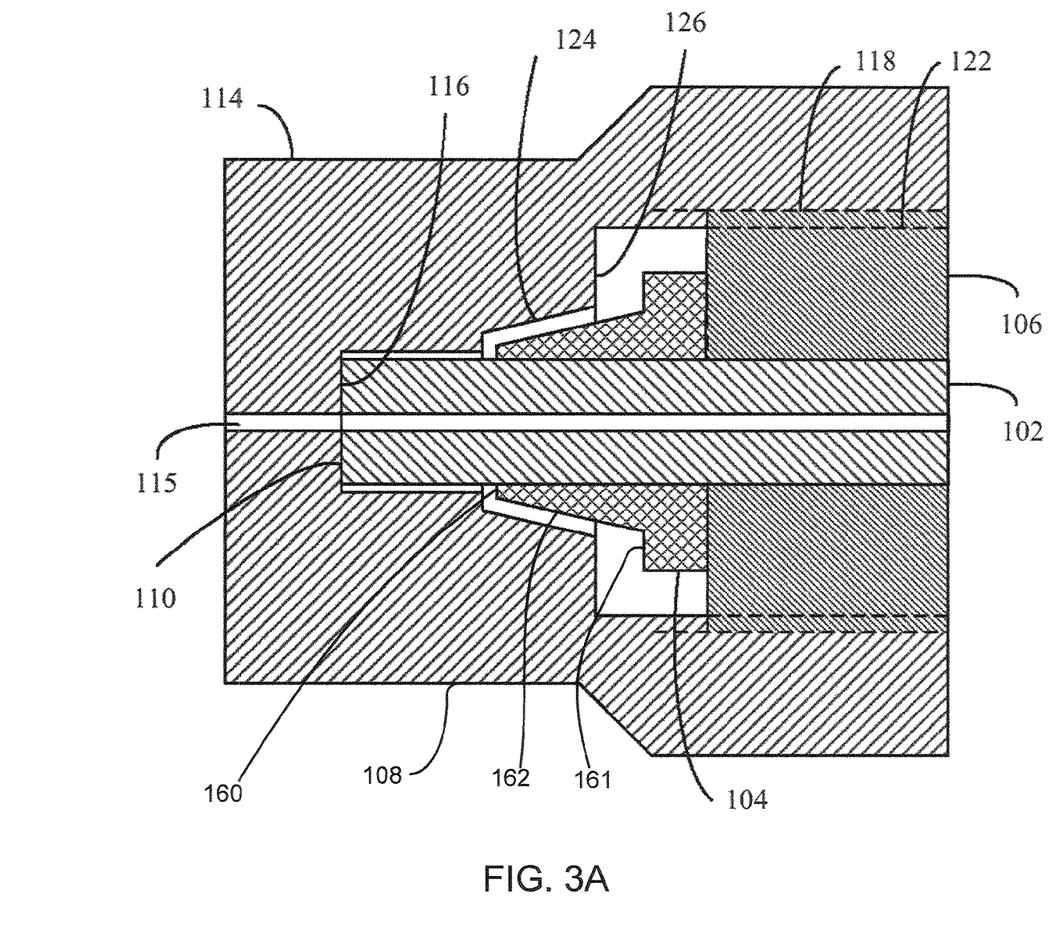
FIG. 3A is a partially enlarged cross-sectional view taken along circle A in FIG. 2, illustrating an exemplary fluidic connection system in a mounting state in accordance with the present application.
Figure 3B:
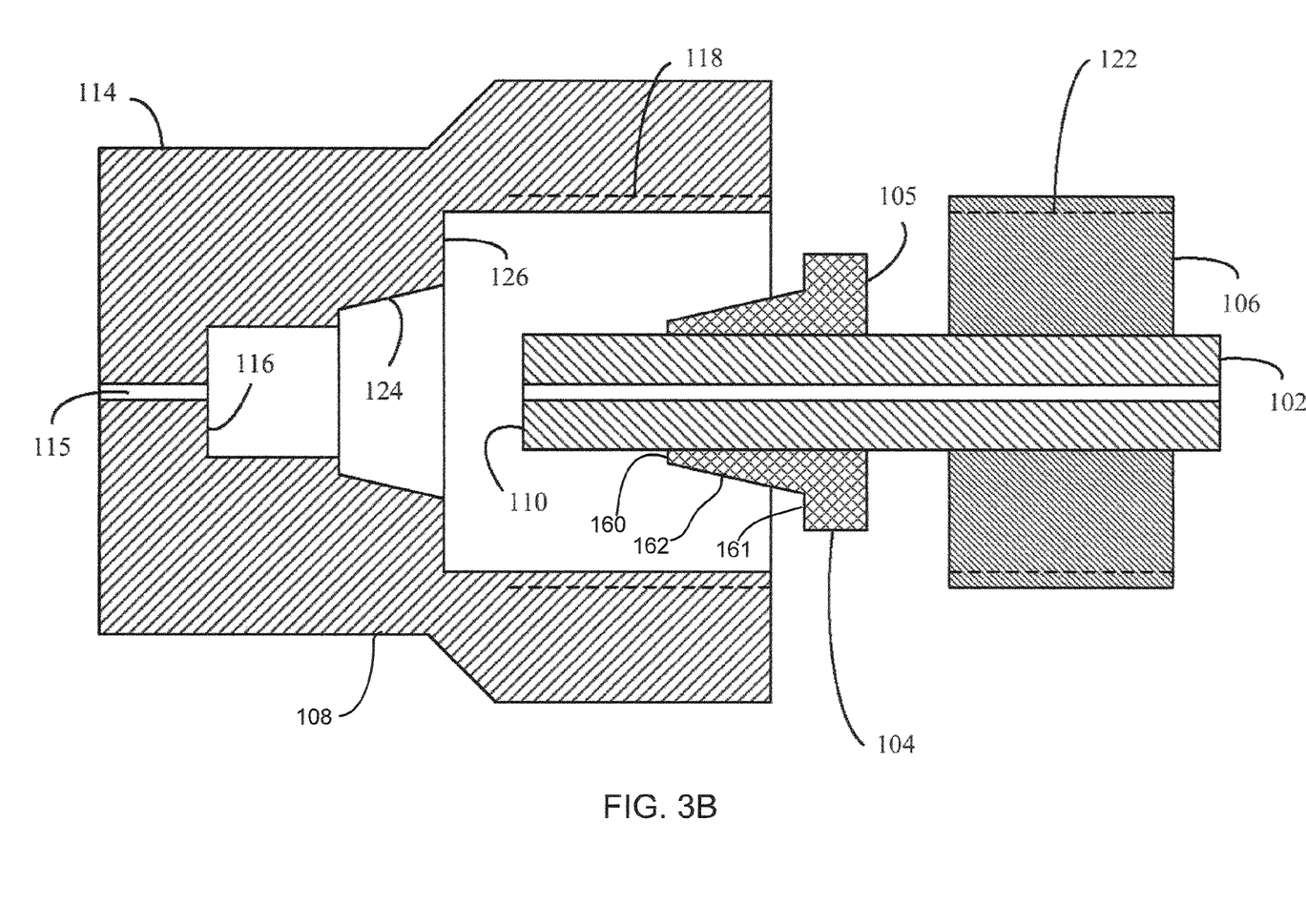
FIG. 3B is a partially enlarged cross-sectional view taken from circle A in FIG. 2, illustrating an exemplary fluidic connection system in a dismounting state in accordance with the present application.

Referring to FIGS. 1-3, there is depicted an exemplary fluidic connection system 100 for use in chromatography, especially for high-performance liquid chromatography. The fluidic connection system 100 in general comprises a capillary tube 102, a flange 104, and a fitting nut 106. The capillary tube 102 includes a front end face 110, and the flange 104 is affixed on the capillary tube 102 at a distance, indicated by L1 in FIG. 1B, from the front end face 110. The fitting nut 106 is slidably coupled with the capillary tube 102 behind the flange 104 so that the fitting nut 106 can be used to push the flange 104 forward when desired. Collectively, the capillary tube 102, the flange 104, and the fitting nut 106 form a plug 101. In various embodiments, the fluidic connection system 100 may further comprise a port 108. The plug 101 removably connects with the port 108 and sealingly engages with the port 108.

Herein, a port refers to any suitable fluidic inlet or outlet of a component used in chromatography and other analytical systems, including bushings, sockets, columns, connectors or the like. It can be made of any suitable materials including polymeric materials or metals, and can be configured to have any suitable geometries including but not limited to standard shapes and sizes. Typically, the port 108 may include a capillary tube receptacle, such as the capillary tube receptacle 114 depicted in FIGS. 2 and 3. The capillary tube receptacle 114 houses a port capillary tube 115 and includes an end seal face 116 and a threaded wall 118. Preferably, the threaded wall 118 is internal. The capillary tube receptacle 114 may further include other additional or optional features. By way of illustration, FIGS. 2 and 3 depicts the capillary tube receptacle 114 including a conical side wall 124 and a shoulder 126.

To achieve a zero dead volume seal, it is essential to have an air-tight or liquid-tight sealing realized across the surface area between the front end face 110 of the capillary tube 102 and the end seal face 116 of the capillary tube receptacle 114 when the plug 101 is pressed into the port 108. That is, the front end face 110 of the capillary tube 102 is required to directly abut and sealingly engage with the end seal face 116 of the capillary tube receptacle 114 when the plug 101 is pushed or pressed into the port 108.

The exemplary connection system 100 of the present application achieve such a zero dead volume seal by affixing the flange 104 on the capillary tube 102 at the distance L1 from the front end face 110. The distance L1 is specified and controlled related to the port 108 so that when the plug 101 and the port 108 are engaged for seal, a most front face 160 of the flange 104 will not touch, rest on or bias against the port 108. Specifically, the most front face 160 will not touch, rest on or bias against the conical side wall 124 or the shoulder 126 of the port 108. Consequently, the front end face 110 of the capillary tube 102 abuts the end seal face 116 of the capillary tube receptacle 114 as the flange 104 is pushed forward, for example, by the fitting nut 106, resulting in a zero dead volume seal.

Depending on the configuration of the port 108, the flange 104 may be constructed accordingly to have any suitable configurations, ensuring that the most front face 160 of the flange 104 will not touch, rest on or bias against the port 108 when the plug 101 and the port 108 are engaged for seal. For example, as illustrated in FIGS. 3A-3B, a conically-shaped flange with a protruded base may be preferred for engaging the port 108 with the conical side wall 124 and the shoulder 126. Additionally, an annular flange with a flat rear face 105 and extending axially may be preferred, because it provides enough surface area and strength for receiving a force from the fitting nut 106. Further, such a flange enables a more even or uniform transfer of the force exerted on the flat rear face 105 to the capillary tube 102 and thus pushes the front end face 110 of the capillary tube 102 forward substantially in the longitudinally or axial direction. However, one would appreciate that the flange 104 can be configured with any suitable size, shape or with variations in other configuration parameters, as long as the most front face 160 of the flange 104 does not rest on or bias against the port 108 when the plug 101 and the port 108 are engaged for seal.

The flange 104 may be made of any suitable materials, including plastics, metals, polymeric or silicone materials. For some applications, the flange 104 may be made of a material preferably comprising PEEK. The material can be clear, natural or black. In addition, the flange 104 may be affixed on the capillary tube 102 by any suitable methods, and may be at a spot or extend circumferentially around the capillary tube 102. Non-limiting examples of suitable affixation methods may include welding for example by laser welding, bonding using adhesives such as epoxy, molding the flange 104 onto or toward the end of the capillary tube 102, crimping or threading the flange 104 onto the capillary tube 102, and monolithically forming the flange and the tube.

In addition, flange 104 may include two or more interlocking pieces, which when assembled lock together and grip the tubing. Such interlocking pieces may be in the form of a Swagelok® ferrule style flange and be configured such that the user can affix the flange to the tubing at the laboratory without requiring assembly at a manufacturing line.

FIG. 1B illustrates the fixation of the flange 104 by laser welding, indicated by arrow 112, from the flat rear face 105 and welded on a spot or circumferentially around the capillary tube 102. Laser welding is a modern and innovative processing technology for various materials including polymers, because it can deliver high values of irradiance to selected area and thus produce localized heating and formation of melt-pool. In various embodiments, materials for the flange 104 or the capillary tube 102 may be black or colored with additives, pigments or material sensitizers to help absorbing laser energy. Alternatively, an absorbing interlayer may be placed in between the flange 104 and the capillary tube 102 for assisting the absorption of laser energy if both the flange 104 and the capillary tube 102 are made of clear materials. A detailed description of the laser welding technology can be found, for example, in a publication by BASF Corporation, entitled "Innovation Innovations in Laser Welding of Thermoplastics: This Advanced Technology is Ready to be Commercialized", 2002-01-2011, the entirety of which is incorporated herein by reference.

Controlling of the distance L1 may be carried out by affixing the flange 104 on the capillary tube 102 first and then cutting the capillary tube 102 at the specified distance L1. After cutting, the front end face 110 is formed on the front of the capillary tube 102. An apparatus disclosed in U.S. Patent Application No. 2011/0173786 may be used for cutting the capillary tube 102, the entirety of which is incorporated herein by reference. The capillary tube 102 may also be cut by lasers. Lasers are widely used in industry as cutting tools due to their ultra flexibility of the cutting conditions, high quality end product, quick set up, non-mechanical contact between the workpiece and the tool, and small size of the heat affected zone.

L1 may be defined or measured as the distance from the front end face 110 of the capillary tube 102 to the rear face 105 of the fitting nut 106, as illustrated in FIG. 1B. One would appreciate that there are various other ways to define and control the distance L1. For example, it may be defined as the distance between the front end face 110 of the capillary tube 102 and the most front face 160 of the flange 104 as indicated by L1' in FIG. 1C, or as the distance between the front end face 110 of the capillary tube 102 and any suitable intermediate face 161 of the flange 104 as indicated by L1" in FIG. 1C.

Figure 7:
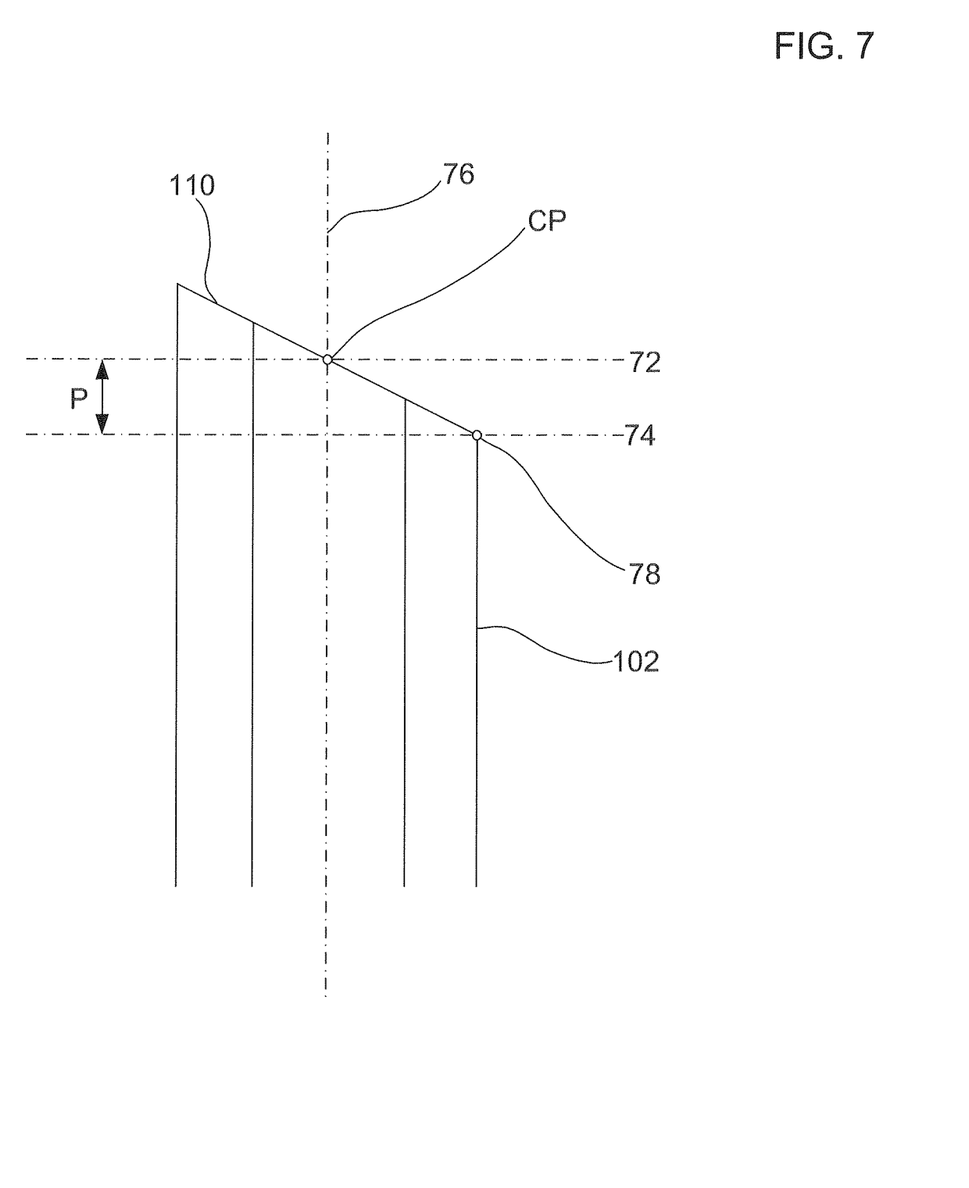
FIG. 7 illustrates a side cross-sectional view of a capillary tube and a perpendicularity of a front face.

The distance L1, L1' or L1" may be tightly controlled based on the buckling strength of the material used in the capillary tube 102 and the thread strength of the materials used in the fitting nut 106 and port 108. For example, L1' distance and tolerance may be derived to insure the shortest tube protrusion for the highest buckling strength and to insure a most front face 160 of the flange 104 does not hit any geometry in the port 108. L1" may be derived to insure full thread engagement between the port 108 and the fitting nut 106 for maximum system pressure strength resistance. One would appreciate that L1, L1' or L1" may be determined or readily varied depending on applications, material properties, processing parameters, or other factors. However, no matter how L1, L1' or L1" is determined or varied, the most front face 160 of flange 104 is ensured not to touch the port 108 when the plug 101 and the port 108 are engaged for seal. Specifically, the most front face 160 of the flange 104 is ensured not to touch, rest on or bias against the conical side wall 124. In addition, the intermediate face 161 of the flange 104 is ensured not to touch, rest on or bias against the shoulder 126 of the port 108. This allows all off the biasing force to be transferred to the front end face 110 of the capillary tube 102. As a result, a zero dead volume seal can be realized on the front end face 110 of the capillary tube 102 abutting the end seal face 116 of the capillary tube receptacle 114. It should be noted that the tapered portion 162 of flange 104 is configured to touch the conical side wall 124 in a non-sealing manner. The tapered portion 162 helps guide front end face 110 of the capillary tube 102 to end seal face 116 of the capillary tube receptacle 114 to ensure that the inner diameters of both capillary tubes are coaxially arranged. In addition to controlling the distance L1, L1' or L1", the front end face 110 of the capillary tube 102 may be precision cut to a desired perpendicularity and surface finish to achieve a better or optimal seal. In the present application, the term "perpendicularity" (P) is based on a distance between two lines (72 and 74) as illustrated in FIG. 7. A first line 72 extends outwardly from a center point CP of front face 110 and is perpendicular to a longitudinal axis 76 of the capillary tube 102. A second line 74 extends outwardly from the longitudinal axis 76 in a perpendicular manner to a point 78 along the periphery of front face 110. The perpendicularity P is a distance from the first line 72 and a second line 74 that provides a maximum separation between the two lines. An optimal front face 110 will have a perpendicularity of zero where all possible second lines will be in the same plane. Actual values for perpendicularity and surface finish may be dependent on various factors, including the materials used for the capillary tube 102 and the port 108, and system pressure. For the capillary tube 102 made of PEEK, Perpendicularity may need to be ≤0.0005 inches and surface finish ≤16 microns. The finish value represents one standard deviation based on the variations in surface height. Alternatively, flatness and surface finish may be used to characterize a cut.

The capillary tube 102 may be rigid or flexible, and may be made of any suitable materials. Example materials for forming the capillary tube 102, the flange 104, the fitting nut 106 and the port 108 include, metals, ceramics, composites and, polymeric materials. More specific examples of materials that can be used to form the capillary tube 102, the flange 104, the fitting nut 106 and the port 108 include polymeric materials such as Polyaryetherketones (PAEK), polyetheretherketone (PEEK), polyimide (PI), polytetrafluoroethylene (PTFE), ethylene-chlorotrifluorethylene (ECTFE), polyphenylsulfone (PPSU), ismaprene, fluoroethylene-propylene (FEP), perfluoralkoxy (PFA), ethylene-tetrafluoroethylene-copolymer (ETFE), polyetherimide (PEI), polyamideimide (PAI), polyphenylene sulfide (PPS), polysulfone (PSU), polypropylene, polyvinylfluoride (PVF), polyvinylidene-fluoride (PVDF), polyetherimide (PEI), polyetheretherketone with fused silica, polychlorotrifluoroethylene (PCTFE), polyoxymethylene, and acetyl polyoxy-methylene. For ion chromatography, polymeric materials, for example PEEK, that can withstand high pressure are preferred over metals or silicon materials.

The capillary tube 102 can have any suitable inner and outer diameter, as long as they are correlated to the shape and size of the port 108. Specifically, the inner diameter of the capillary tube 102 and the port capillary tube 115 may be essentially the same to ensure a zero dead volume seal for enhancing chromatographic performance such as minimization of peak band dispersion. Examples of suitable outer diameters include those in a range of about 1/32 inch to about 1/2 inch (0.7937 millimeters to 12.69 millimeters) and include the standard outer diameter of about 1/32 inch (0.7937 millimeters), 1/16 inch (1.587 millimeters), 1/8 inch (3.174 millimeters), 1/4 inch (6.34 millimeters), and 1/2 inch (12.69 millimeters). The inner and/or outer diameter may be limited by buckling strength of the capillary tube 102, system pressure to be sealed, or other factors. In a non-limiting embodiment as illustrated in FIGS. 1B and 1C, L1 may be about 0.197 inches, L1' may be about 0.089 inches, and L1" may be about 0.162 inches where the PEEK tubing has an ID of about 0.0025 inches and an OD of about 0.062 inches.

Figure 4A:
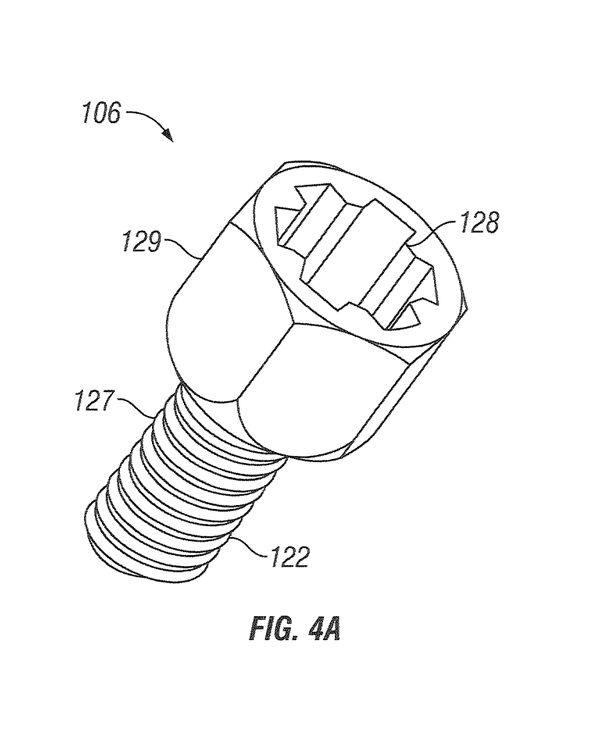
FIG. 4A illustrates a perspective view of an exemplary fitting nut in accordance with the present application.
Figure 4B:
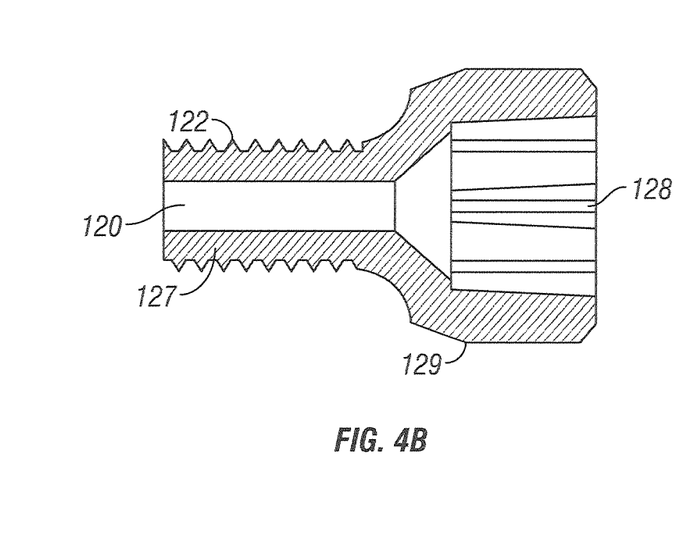
FIG. 4B illustrates a cross-sectional view of an exemplary fitting nut in accordance with the present application.
Figure 5A:
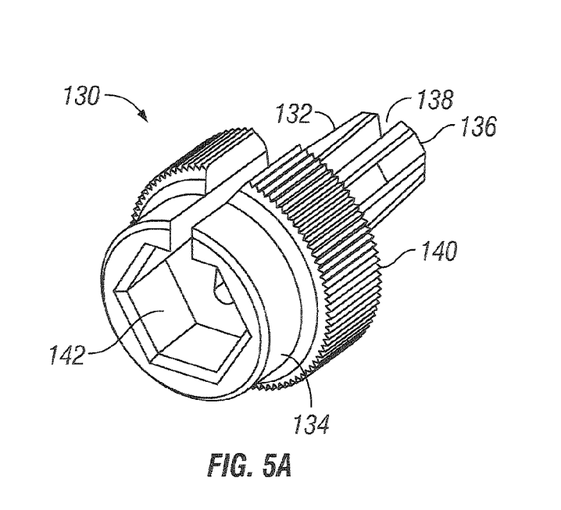
FIG. 5A illustrates a rear perspective view of an exemplary insert tool in accordance with the present application.
Figure 5B:
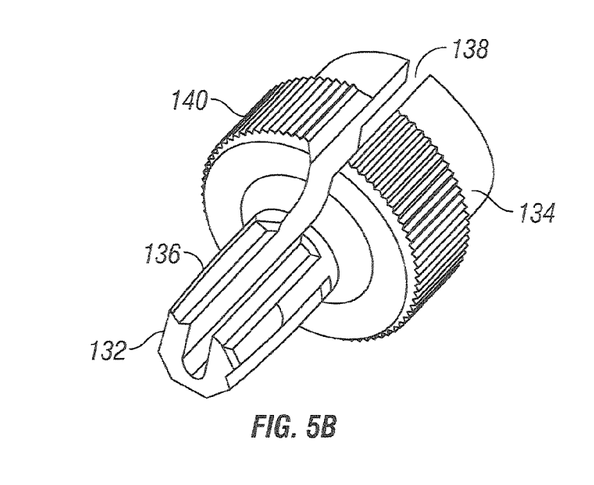
FIG. 5B illustrates a front perspective view of an exemplary insert tool in accordance with the present application.
Figure 5C:
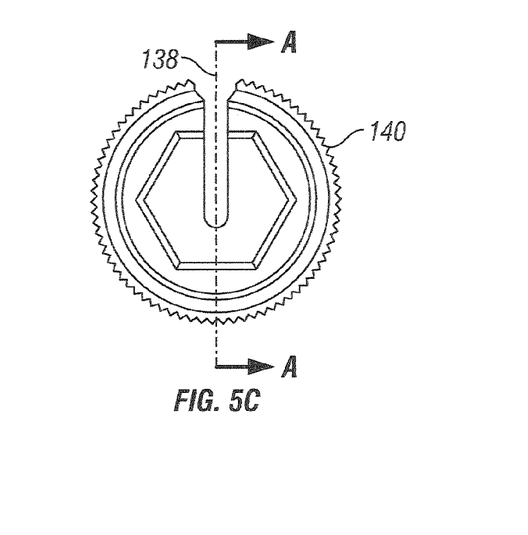
FIG. 5C illustrates a back view of an exemplary insert tool in accordance with the present application.
Figure 5D:
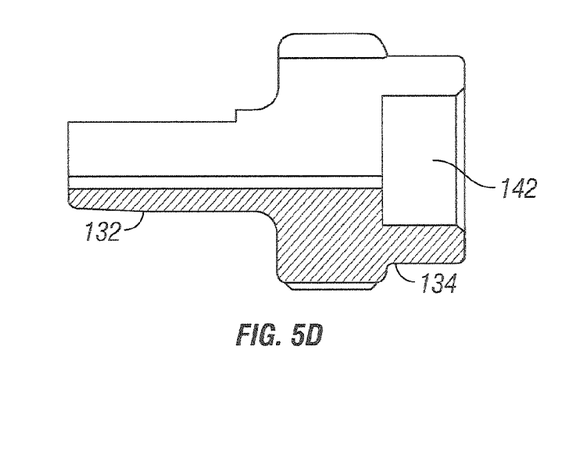
FIG. 5D illustrates a cross-sectional view of an exemplary insert tool taken along line A-A in FIG. 5C in accordance with the present application.

Referring now to FIGS. 4A-4B, there is depicted an exemplary fitting nut 106 comprising a threaded portion 127 and a head 129. The head 129 may have a shape of, for example, hexagon or other suitable geometries that can be used for tightening. An axial hole 120 is configured throughout the fitting nut 106 to allow the capillary tube 102 pass through and may be essentially along the central axis of the fitting nut 106. Preferably, the axial hole 120 has an inner diameter that is larger in the head 129 than in the threaded portion 127, which in turn is slightly larger than the outer diameter of the capillary tube 102. With such a slightly larger diameter, the threaded portion 127 may help align the capillary tube 102 with the port 108. A threaded wall 122 is formed on the outer peripheral wall of the threaded portion 127. The threaded wall 122 matches the threaded wall 118 formed in the capillary tube receptacle 114 so that the fitting nut 106 and the capillary tube receptacle 114 are rotatably relative to each other. To engage the plug 101 with the port 108 for seal, the exemplary fitting nut 106 is turned in one direction and pushes the flange 104 until the front end face 110 of the capillary tube 102 abuts the end seal face 116 of the capillary tube receptacle 114. To release the plug 101 from the port 108, the exemplary fitting nut 106 is turned in an opposite direction.

In various embodiments, the exemplary fitting nut 106 may further comprise an internal spline 128, a hex, or other features for assisting the rotation of the fitting nut 106. The internal spline 128 is formed in the head of the fitting nut 106, extending inwardly. The inward extension of the internal spline 128 may be substantially along the axis or may be slanted to form an angle with the axis of the fitting nut 106. In some cases, the internal spline 128 may be even curvy, or any other appropriate geometries. By way of illustration, FIGS. 4A-4B depict a substantially straight internal spline 128. The fitting nut 106 with an internal spline 128 is advantageous in many ways, in particular, for assisting proper installation of the plug 101 when multiple ports are in close proximity, such as in an inject valve.

In addition, to further facilitate the proper installation of the plug 101, the exemplary connection system 100 may comprise a corresponding insertion tool, such as the exemplary insertion tool 130 depicted in FIGS. 5A-5D. As shown, the exemplary insertion tool 130 comprises a spline portion 132 and a relatively larger head 134. The spline portion 132 is configured to be able to engage with the head 129 of the fitting nut 106, and may include an external spline 136 that is complementary to the internal spline 128 formed in the head 129 of the fitting nut 106. The head 134 of the insertion tool 130 may be formed with a knurling 140 on its outer periphery or on a portion of its outer periphery to facilitate a better gripping of the insertion tool 130 by a user or other tools.

In various embodiments, the exemplary insertion tool 130 may further comprise a radial slot 138. The radial slot 138 allows the insertion tool 130 to be pushed onto the capillary tube 102 from the side and engage with the fitting nut 106. The insertion tool 130 may be similar or have similar features as the device disclosed in U.S. Pat. No. 8,037,788, the entirety of which is incorporated herein by reference. The torque limitation function may be in the knurled head, and torque may be limited by a ball plunger in the slot design or a spring loaded ratchet/pawl mechanism. In an embodiment, the torque limitation setting may range from about 25 oz-in to about 30 oz-in.

The torque limiter in accordance with the present invention has many advantages. For example, it ensures a proper or perfect engagement of the plug 101 with the port 108, neither loose nor tight. As a result, it prevents potential damages to the plug 101 and/or the port 108, specifically to the capillary tube 102 of the plug 101, and more specifically to the front end face 110 of the capillary tube 102. At the same time, the torque limiter in according with the present invention provides a capability to ensure that a zero dead volume seal or an optimal seal is achieved.

Additionally, the exemplary insertion tool 130 may comprise a bore 142 formed in the head 134 of insertion tool 130. By way of illustration, FIGS. 5A-5D depicts a hexagonal bore 142. One would appreciate that configuration of the bore can vary in accordance with the present application. For example, the bore 142 may be configured to have a triangular or a square cross section. The configuration of the bore 142, including shapes and sizes, may depend on the materials used for making the insertion tool 130, the strength required for the insertion tool 130, the limiting torque or torque range for optimal seal, or other factors. One would appreciate that the insertion tool 130 may include other optional, additional or alternative features.

Compared to conventional connection systems, connection systems of the present application provide many advantages. For example, exemplary connection systems have a zero dead volume seal between the plug and the port, reducing or eliminating the peak broadening. Exemplary connection systems also ensure a leakage free connection of the plug and the port. Furthermore, exemplary connection systems work without a ferrule, eliminating the creation of extra-column volumes due to incorrect positioning of the ferrule or due to slipping off the capillary tube when subjected to high pressures. Without a ferrule, exemplary connection systems are easy to install and align.

Having connection systems with zero dead volume and leakage free seals are highly desirable, particularly for chromatography. In chromatography, liquids or gases are fed through connection lines between various components. To create tight connection, these connection lines typically incorporate a connection system at an end. Any dead volume or leakage in the connection system would adversely impact the chromatographic performance of the system. For example, presence of dead volume in a connection system would broaden the band dispersion. Having connection systems with zero dead volume and leakage free seal is especially critical to high performance liquid chromatography (HPLC). It is because HPLC generally involves higher pressure and capillary flow, and it is very difficult to detect leakages at capillary flow rates.

Figure 6:
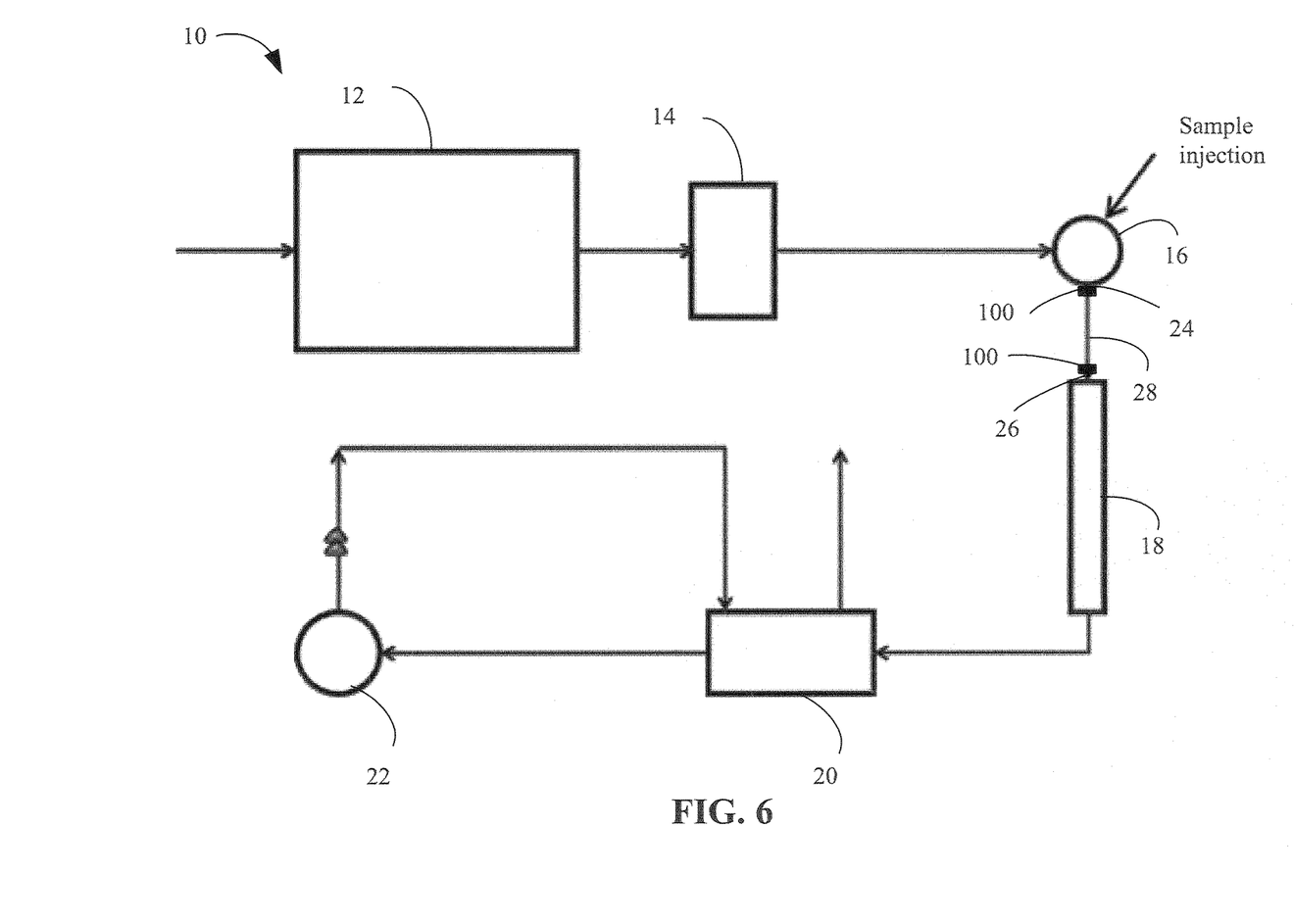
FIG. 6 illustrates a chromatography system in which an exemplary connection system in accordance with the present application is used.

Connection systems of the present disclosure can be used in a variety of systems including HPLC, mass spectrometry (MS), or LC-MS. As a non-limiting example, FIG. 6 illustrates the use of the present connection systems in ion chromatography. As shown, the ion chromatography system 10 in general includes a separation means such as a column 18 and a detection means such as a conductivity cell 22. The column 18 chromatographically separates sample ions, and the conductivity cell 22 detects the resolved ionic species. The system 10 may further include a pump 12 for pumping deionized water, an eluent generator 14 for generating the eluent, a sample injection valve 16 for injecting the sample, and a suppressor 20 for suppressing the conductivity of the electrolyte of the eluent. By way of illustration, FIG. 6 depicts the system including two present connection systems 100, one at an outlet 24 of the sample injection valve 16 and the other at an inlet 26 of the column 18. In such configuration, the outlet 24 of the sample injection valve 16 and the inlet 26 of the column 18 may serve as the port 108, while the line 28 may be a capillary tube having a flange 104 and a fitting nut 106 at each end for connecting the sample injection valve 16 with the column 18. One would appreciate that the connection systems 100 of the present disclosure can be used along with any other connection lines to connect any two of these components in the system 10. One would also appreciate that a connection line does not need to have the present connection system 100 at both ends. It can have only one connection system 100 at one end.

For convenience in explanation and accurate definition in the appended claims, the terms "front" or "rear", "inner" or "outer", "forward" or "backward", and etc. are used to describe features of the exemplary embodiments with reference to the positions of such features as displayed in the figures.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. A fluidic connection system for use in chromatography, comprising:
   a port including a capillary tube receptacle with an end seal face and a threaded wall;
   a capillary tube including a front end face for sealingly abutting against the end seal face of the port;
   a flange affixed on the capillary tube at a distance L1 from the front end face of the capillary tube; and
   a fitting nut including an axial hole to allow the capillary tube to pass therethrough and a matching threaded wall corresponding to the threaded wall of the port, the fitting nut slidably coupled with the capillary tube behind the flange,
   wherein the distance L1 is predetermined such that when the flange is pushed forward by the fitting nut, the front end face of the capillary tube abuts directly against the end seal face of the port.

2. The fluidic connection system of claim 1, wherein the flange is affixed on the capillary tube by welding.

3. The fluidic connection system of claim 1, wherein the flange is circumferentially affixed on the capillary tube.

4. The fluidic connection system of claim 1, wherein the flange includes a flat rear face.

5. The fluidic connection system of claim 1, wherein the flange is made of a material comprising PEEK.

6. The fluidic connection system of claim 1, wherein a distance L1' is defined as being between the front end face of the capillary tube and a most front face of the flange, in which the most front face of the flange does not touch the port.

7. The fluidic connection system of claim 6, wherein the most front face of the flange does not touch the port when the flange is pushed forward by the fitting nut, or when the front end face of the capillary tube contacts the end seal face of the port.

8. The fluidic connection system of claim 1, wherein the capillary tube is made of a material comprising PEEK.

9. The fluidic connection system of claim 1, wherein the capillary tube has an outer diameter of about 1/16 inch.

10. The fluidic connection system of claim 1, wherein the front end face of the capillary tube has a perpendicularity of ≤0.0005 inches to a longitudinal axis of the capillary tube.

11. The fluidic connection system of claim 1, wherein the front end face of the capillary tube has a surface finish of ≤16 microns.

12. The fluidic connection system of claim 1, wherein the fitting nut includes an internal spline formed in a head of the fitting nut for facilitating a rotation of the fitting nut.

13. The fluidic connection system of claim 12, further comprising an insertion tool for rotating the fitting nut, wherein the insertion tool includes an external spline corresponding to the internal spline formed in the fitting nut.

14. The fluidic connection system of claim 13, wherein the insertion tool further includes a radial slot for allowing the insertion tool to be pushed onto the capillary tube from a side.

15. The fluidic connection system of claim 14, wherein the insertion tool includes a torque limiter to insure proper seal force for the end face of the capillary tube.

16. The fluidic connection system of claim 13, wherein the insertion tool further includes a knurling formed on an outer periphery or on a portion of the outer periphery of the insertion tool for assisting gripping of the insertion tool.

17. The fluidic connection system of claim 13, wherein the insertion tool further includes a bore formed in a head of the insertion tool.

18. A plug for removably connecting a port with an end seal face, the plug comprising:
   a capillary tube including a front end face for sealingly abutting against the end seal face of the port;
   a flange affixed on the capillary tube at a distance L1 from the front end face of the capillary tube; and
   a fitting nut including an axial hole to allow the capillary tube to pass therethrough and a matching threaded wall corresponding to a threaded wall of the port, the fitting nut slidably coupled with the capillary tube behind the flange,
   wherein the distance L1 is predetermined such that when the flange is pushed forward by the fitting nut, the front end face of the capillary tube abuts directly against the end seal face of the port.

19. A chromatography system comprising:
   a device including a port, wherein the port includes a capillary tube receptacle with an end seal face and a threaded wall; and
   a connection line including a plug at one end for removably connecting the port in the device, wherein the plug includes:
   a capillary tube including a front end face for sealingly abutting against the end seal face of the port;
   a flange affixed on the capillary tube at a distance L1 from the front end face of the capillary tube; and
   a fitting nut including an axial hole to allow the capillary tube to pass therethrough and a matching threaded wall corresponding to a threaded wall of the port, the fitting nut slidably coupled with the capillary tube behind the flange;
   wherein the distance L1 is predetermined such that when the flange is pushed forward by the fitting nut, the front end face of the capillary tube abuts directly against the end seal face of the port.

20. The chromatography system of claim 19, further comprising at least one of an eluent generator, a sample injection valve, a column, a suppressor, or a detector.

* * * * *